US011986632B2

(12) United States Patent
Burgess et al.

(10) Patent No.: US 11,986,632 B2
(45) Date of Patent: May 21, 2024

(54) SECURE PATIENT-CONTROLLED ANALGESIA

(71) Applicant: CareFusion 303, Inc., San Diego, CA (US)

(72) Inventors: Brendan John Burgess, Poway, CA (US); Edward Stephen Ferner, Escondido, CA (US); Beth A. Schneider, San Diego, CA (US); Shannon John Johnson, Doral, FL (US); Daniel M. Abal, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 254 days.

(21) Appl. No.: 17/320,057

(22) Filed: May 13, 2021

(65) Prior Publication Data

US 2021/0361863 A1 Nov. 25, 2021

Related U.S. Application Data

(60) Provisional application No. 63/027,261, filed on May 19, 2020.

(51) Int. Cl.
*A61M 5/172* (2006.01)
*A61M 5/14* (2006.01)

(52) U.S. Cl.
CPC ... *A61M 5/1723* (2013.01); *A61M 2005/1405* (2013.01); *A61M 2205/3303* (2013.01); *A61M 2205/505* (2013.01); *A61M 2205/609* (2013.01); *A61M 2230/04* (2013.01); *A61M 2230/10* (2013.01); *A61M 2230/20* (2013.01); *A61M 2230/30* (2013.01); *A61M 2230/42* (2013.01); *A61M 2230/63* (2013.01)

(58) Field of Classification Search
None
See application file for complete search history.

(56) References Cited

U.S. PATENT DOCUMENTS 5,681,285 A 10/1997 Ford et al.
5,713,856 A 2/1998 Eggers et al.
(Continued)

OTHER PUBLICATIONS

International Search Report and Written Opinion for Application No. PCT/US2021/033017, dated Aug. 30, 2021, 13 pages.

*Primary Examiner* — Manuel A Mendez
(74) *Attorney, Agent, or Firm* — Morgan, Lewis & Bockius LLP

(57) ABSTRACT

A system and method for operating an analgesia administration system is disclosed. A control device is associated with a drug delivery device and configured to receive a first user input including at least a portion of a fingerprint of a patient, together with a second user input corresponding to a request to administer medication. The portion of the fingerprint is compared with previously-stored fingerprints to determine an identity of the patient and, in response to receiving the second user input and determining that the patient is an authorized user, one or more sensors are used to obtain one or more signals indicative of a state of the patient. If the state of the patient satisfies a set of medication delivery criteria, the drug delivery device is caused to administer a predefined amount of medication to the patient.

20 Claims, 6 Drawing Sheets

(56) References Cited

U.S. PATENT DOCUMENTS

| | | |
|---|---|---|
| 7,871,394 B2 | 1/2011 | Halbert et al. |
| 2005/0177096 A1 | 8/2005 | Bollish et al. |
| 2010/0174229 A1* | 7/2010 | Hsu .................. A61M 5/142 |
| | | 340/5.82 |
| 2016/0095976 A1 | 4/2016 | Simpson et al. |
| 2020/0051190 A1 | 2/2020 | Kamen et al. |
| 2021/0043295 A1 | 2/2021 | Macoviak et al. |

* cited by examiner

SECURE PATIENT-CONTROLLED ANALGESIA

CROSS REFERENCE TO RELATED APPLICATIONS

This application is a nonprovisional of U.S. Provisional Application Ser. No. 63/027,261, entitled "SECURE PATIENT-CONTROLLED ANALGESIA," filed on May 19, 2020, the entirety of which is incorporated herein by reference.

TECHNICAL FIELD

This application relates generally to operating a medical device.

BACKGROUND

Patient-Controlled Analgesia (PCA) is a commonly-used method to relieve pain experienced by a patient. The method typically involves using a syringe pump that is programmed to allow a delivery of the analgesia only when the patient desires it. For example, the patient can press a button on a PCA control device when they desire to administer a predetermined bolus of the analgesia. This way, if the patient does not push the button, no analgesia is administered.

However, in some situations, a person other than the patient may accidentally operate the PCA control device without the patient's knowledge (e.g., risk of "PCA by proxy"). Therefore, a method and device for ensuring that the patient has exclusive control of the PCA control device are highly desired.

SUMMARY

According to various aspects, the subject technology includes a system, comprising: a drug delivery device; a drug control device operably connected to the drug delivery device; and a control unit operably connected to the drug delivery device and configured to capture biometric information from a person, wherein the control unit is configured to: determine a medication currently loaded by the drug delivery device; receive, via the drug control device, a request for the drug delivery device to administer a dose of the medication and biometric information captured by the drug control device, confirm, based on the biometric information, that a patient associated with the biometric information is authorized to self-administer the dose of the medication from the drug delivery device; responsive to receiving the request and biometric information and confirmation that the patient is authorized user to self-administer the dose: obtain, by one or more sensors associated with the drug delivery device, one or more signals indicative of a state of the patient; and cause, after determining that the state of the patient satisfies a predetermined criteria for allowing the patient to self-administer the medication, the drug delivery device to administer the dose of the medication to the patient.

In some implementations, the drug control device is a handheld control device, and the request and biometric information are captured within a predetermined period of time of each other. The one or more sensors may be included in the drug control device and activated after the request and biometric information are received by the drug control device.

In some implementations, the drug control device comprises a fingerprint reader and the biometric information comprises at least a portion of a fingerprint. In some implementations, the one or more signals indicative of the state of the patient include: an electroencephalogram (EEG) signal, electrocardiography (ECG) signal, peripheral capillary oxygen saturation (SpO2) signal, respiratory rate signal, or movement signal. In some implementations, determining that the state of the patient satisfies the predetermined criteria includes determining that the patient is in a conscious state based at least in part on the one or more signals.

In some implementations, confirming that the patient is authorized to self-administer the dose comprises: determining an identity of the patient; identifying, from a hospital information system based at least in part on the identity of the patient or an identifier associated drug delivery device, an amount of medication received by the patient over a period of time; and determining that the amount of medication satisfies a threshold amount for the period of time.

In some implementations, the control unit is further configured to: after obtaining the one or more signals indicative of a state of the patient, determining that a discomfort level associated with the patient is greater than a threshold discomfort level based on the one or more signals. In some implementations, the one or more sensors comprise: a motion sensor for detecting movement of the patient; and one or more physiological monitors for measuring a physiological condition, including: heart rate, blood pressure, electrocardiographic signal, electroencephalographic signal, or oxygen level, wherein the control unit is configured to: detect movement of the patient; measure the physiological condition of the patient; and determine the discomfort level based on the detected movement of the patient satisfying a movement threshold and the physiological condition satisfying a physiological threshold. In some implementations, the drug delivery device comprises a control configured to receive a user input to initiate the request, and to determine a magnitude of the user input, and wherein administering, by the drug delivery device, the dose of the medication to the patient includes administering an amount of the medication in accordance with the magnitude of the user input. Other aspects, include corresponding methods, apparatuses, and computer program products for further implementation of the system.

An advantage of using the subject technology for administering medication to a patient is that medication can be administered after a patient (or another authorized person) successfully authenticates using fingerprint biometrics or other trustworthy identifying information. Therefore, the subject technology protects patient safety by eliminating the risk of PCA by proxy because authentication using, for example, fingerprint biometrics cannot be easily copied.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system and method for administering medication to a patient, including a control device associated with a drug delivery device and configured to receive at least a portion of a fingerprint of a patient, together with a request to administer medication. A patient care unit (PCU), or server on behalf of the PCU, compares the at least a portion of the fingerprint with previously-stored fingerprints to determine an identity of the patient and, in response to receiving the request and determining that the patient is an authorized user, obtains (e.g., using one or more sensors) one or more signals indicative of a state of the patient. Responsive to determining that the state of the patient satisfies a first set of medication delivery criteria, the PCU or central server causes the drug delivery device to administer a predefined amount of medication to the patient.

Figure 1:
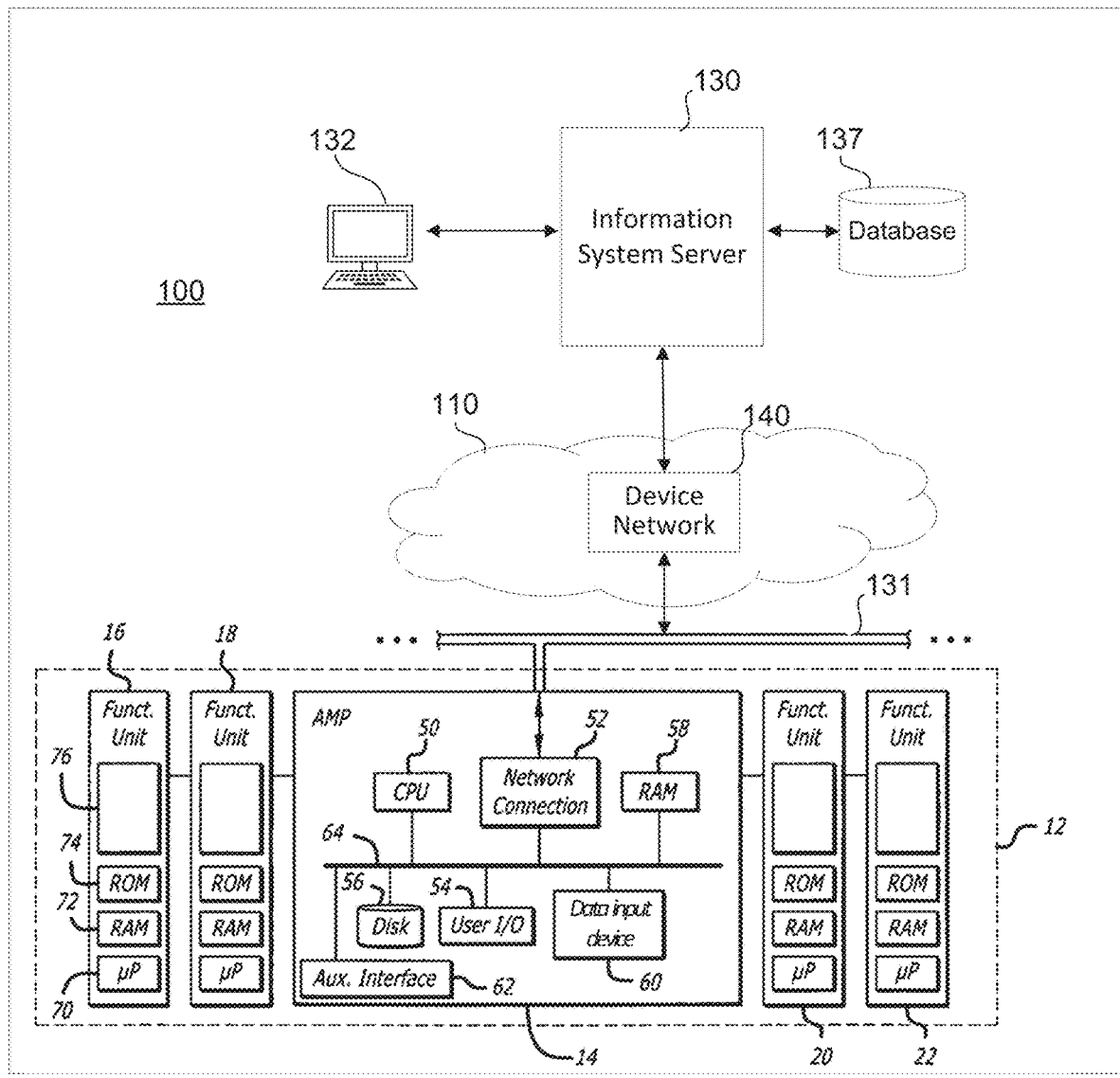
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device (or "medical device" generally) 12 is connected to a healthcare network 110. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), a patient controlled analgesia (PCA) wand, or other similar devices. Each element of patient care device 12 is connected to healthcare network 110 by a transmission channel 131. Transmission channel 131 is any wired or wireless transmission channel, for example, an 802.11 wireless local area network (LAN). In some implementations, healthcare network 110 also includes computer systems located in various departments throughout a hospital. For example, healthcare network 110 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, healthcare network 10 includes a device network 140 by which patient care device 12 (and other devices) communicates in accordance with normal operations. According to some implementations, the devices and supporting services of healthcare network 110 or a portion thereof may be cloud-based with, for example, the servers and services (e.g., databased, APIs, etc.) located remote from the hospital and/or distributed across multiple remote locations or regions.

Additionally, institutional patient care system 100 may incorporate a separate information system server 130, the function of which will be described in more detail below. Moreover, although information system server 130 is shown as a separate server, the functions and programming of information system server 130 may be incorporated into another computer, such as, for example, a hospital information system server or cloud-based server, if such is desired by engineers designing the institution's information system. Institutional patient care system 100 may further include one or multiple device terminals 132 for connecting and communicating with information system server 130. Device terminals 132 may include personal computers, personal data assistant, mobile devices such as laptops, tablet computers, augmented reality devices, or smartphones, configured with software for communications with information system server 130 via healthcare network 110. The information system server 130 may receive and provide information about patient and/or their treatment such as measurements from patient monitoring devices (not shown), entries for the patient via one of the device terminals 132, or events from the patient care device 12.

Patient care device 12 comprises a system for providing patient care, such as that described in U.S. Pat. No. 5,713,856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54 (e.g., a display screen and/or keyboard), a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical devices may be used without departing from the subject technology. Additionally, data input device 60 may be a separate functional module, such as functional modules 16, 18, 20 and 22, and configured to communicate with interface unit 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices associated with interface unit 14 for providing care to a patient or for monitoring patient condition. As shown in FIG. 1, at least one of functional modules 16, 18, 20, 22 may be an infusion pump module such as an intravenous infusion pump for delivering medication or other fluid to a patient. For example, functional module 16 may be an infusion pump module. Each of functional modules 16, 18, 20, and 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. In other examples, functional modules 18, 20 and/or 22 may be a printer, scanner, bar code reader or any other peripheral input, output or input/output device.

Each functional module 16, 18, 20, and 22 communicates directly or indirectly with interface unit 14, with interface unit 14 providing overall monitoring and control of patient care device 12. Functional modules 16, 18, 20, and 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit 14. As described above, additional medical devices or peripheral devices may be connected to patient care device 12 through one or more auxiliary interfaces 62.

Each functional module 16, 18, 20, and 22 may include module-specific components 76, a microprocessor 70, a volatile memory 72 and a nonvolatile memory 74 for storing information. In some implementations, a functional module may include hardware components similar to those of control unit 14 including, but not limited to, a CPU 50 connected to memory RAM 58, one or more interface devices such as user interface device 54, a coded data input device 60, a network connection 52, and an auxiliary interface 62 for communicating with additional modules or devices. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

According to various implementations, while each functional module may be capable of independent operation (e.g., as described with respect to control unit 14 and its hardware components), interface unit 14 is configured to monitor and control overall operation of patient care device 12. For example, control module 14 may provide programming instructions to the functional modules 16, 18, 20, 22 and monitor the status of each module.

Patient care device 12 may be capable of operating in several different modes, or personalities, with each personality defined by a configuration database. Each mode or personality may include a different set of configuration parameters, or implement a different drug library, as described below. The configuration database may be a disk 56 internal to patient care device, or an external database 137. A particular configuration database (or portion thereof) may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 12 location in the hospital or hospital computer network. Patient care information may be entered through interface device 52, 54, 60 or 62, and may originate from anywhere in network 10, such as, for example, from a pharmacy server, admissions server, laboratory server, and the like.

Interface unit 14 of patient care device 12 also has access to a drug library. Further information on drug libraries is contained in U.S. Pat. No. 5,681,285 to Ford, which is incorporated herein by reference in its entirety. The drug library may be resident in the controller, in a local accessible memory, or may be located elsewhere on the system network but be accessible by the controller. "Drug Library Profiles" may be established in which medications (e.g., drugs), concentrations, and other pumping parameters are set particular to that care area—such as, for example, an ICU (intensive care unit) profile, a pediatric profile, a neonatal profile and others. Data sets of medications allowed for use and configurations of pumping parameters including limitations for that use may be available for each drug library profile. As such, drug library profiles may, although not necessarily, correspond to different patient care areas of the hospital. Thus a controller 14 located in a pediatric ward, for example, may utilize a pediatric drug library profile that includes sets of allowed medications, pumping parameters, and pumping limitations that are specific to patients classified as pediatric or located in a pediatric ward. Similarly, a controller 14 located in an ICU may utilize an ICU drug library profile that includes a different set of allowed medications, pumping parameters, and pumping limitations that are specific to patients located in an intensive care environment and other patients requiring intensive care.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and healthcare network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within healthcare network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 2A:
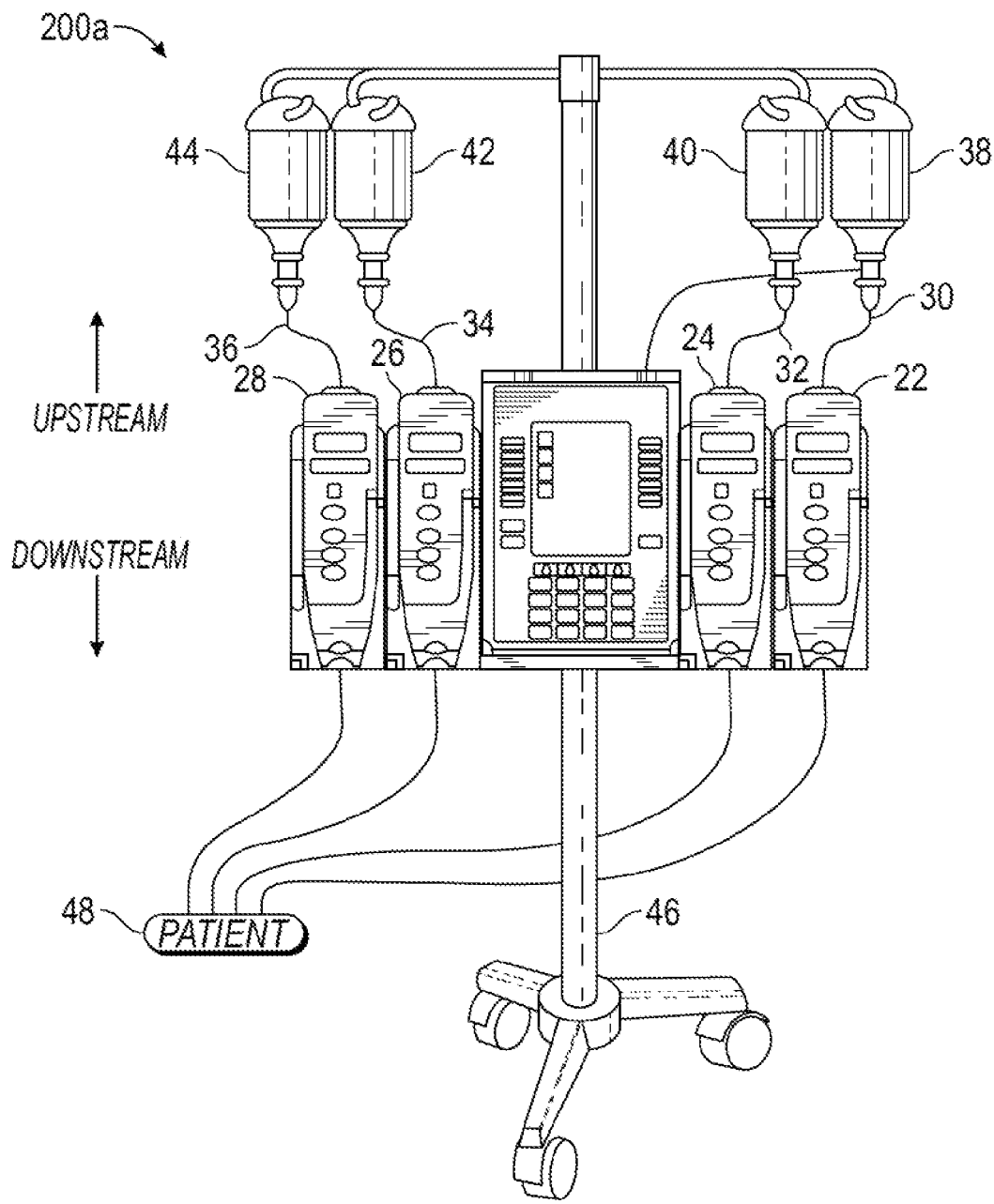
FIG. 2A is an example patient care device that may be interacted with by a clinician or a patient within a healthcare organization, according to aspects of the subject technology.

FIG. 2A is an example patient care device which may be interacted with by a clinician or a patient within a healthcare organization, according to aspects of the subject technology. Patient care device 200 shown in FIG. 2 is similar or identical to patient care device 12 in FIG. 1, including four fluid infusion pumps 22 (e.g., functional module 22 in FIG. 1), 24, 26, and 28 each of which is in operative engagement with a respective fluid administration set 30, 32, 34, and 36. Fluid supplies 38, 40, 42, and 44, which may take various forms but in this case are shown as bottles, are inverted and suspended above the pumps. Fluid supplies may also take the form of bags or other types of containers. Both patient care device 200 and fluid supplies 38, 40, 42, and 44 are mounted to a roller stand or pole 46. The specific fluid supplies as well as their orientation (e.g., mount location, mount height, mounting type, etc.) within the care area may be generate one or more interaction records. The interaction record for a set for example may be generated in part by detecting a scannable code associated with the set prior to use. Once scanned, the interaction record may be recorded for use as described herein.

As shown in the example implementation of FIG. 2A, each administration set 30, 32, 34, and 36 is connected between a respective fluid supply 38, 40, 42, and 44 and a patient 48 so that patient 48 may receive the fluids in all the fluid supplies. The administration set may be identified either actively by, for example, scanning by a clinician or passively by, for example, wireless or optical detection of the administration set. As with the fluid supply, once identified, an interaction record may be generated identifying the administration set and one or more of the clinician, programming module, pump, administration set positioning (e.g., administration location (e.g., left forearm, right upperarm, etc.).

Each of fluid infusion pump 22, 24, 26, and 28 is used to infuse each of the fluids of the fluid supplies into patient 48. Fluid infusion pumps 22, 24, 26, and 28 are flow control devices that will act on the respective tube or fluid conduit of the fluid administration set to move the fluid from the fluid supply through the conduit to patient 48. Because individual pumps are used, each can be individually set to the pumping or operating parameters required for infusing the particular medical fluid from the respective fluid supply into the patient at the particular rate prescribed for that fluid by the clinician. The activities performed by the pump or clinician to infuse the particular medical fluid may be associated with one or interaction which may be recorded and processed as described.

Figure 3:
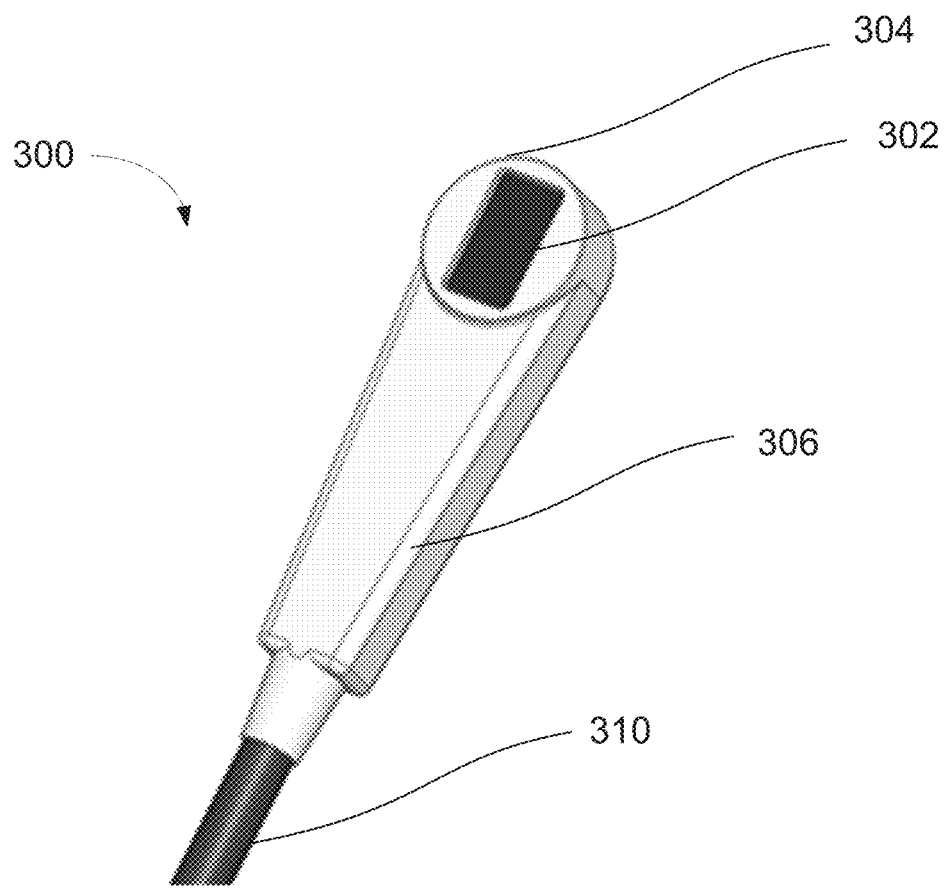
FIG. 3 depicts an example patient-controlled analgesia device, according to aspects of the subject technology.
Figure 4:
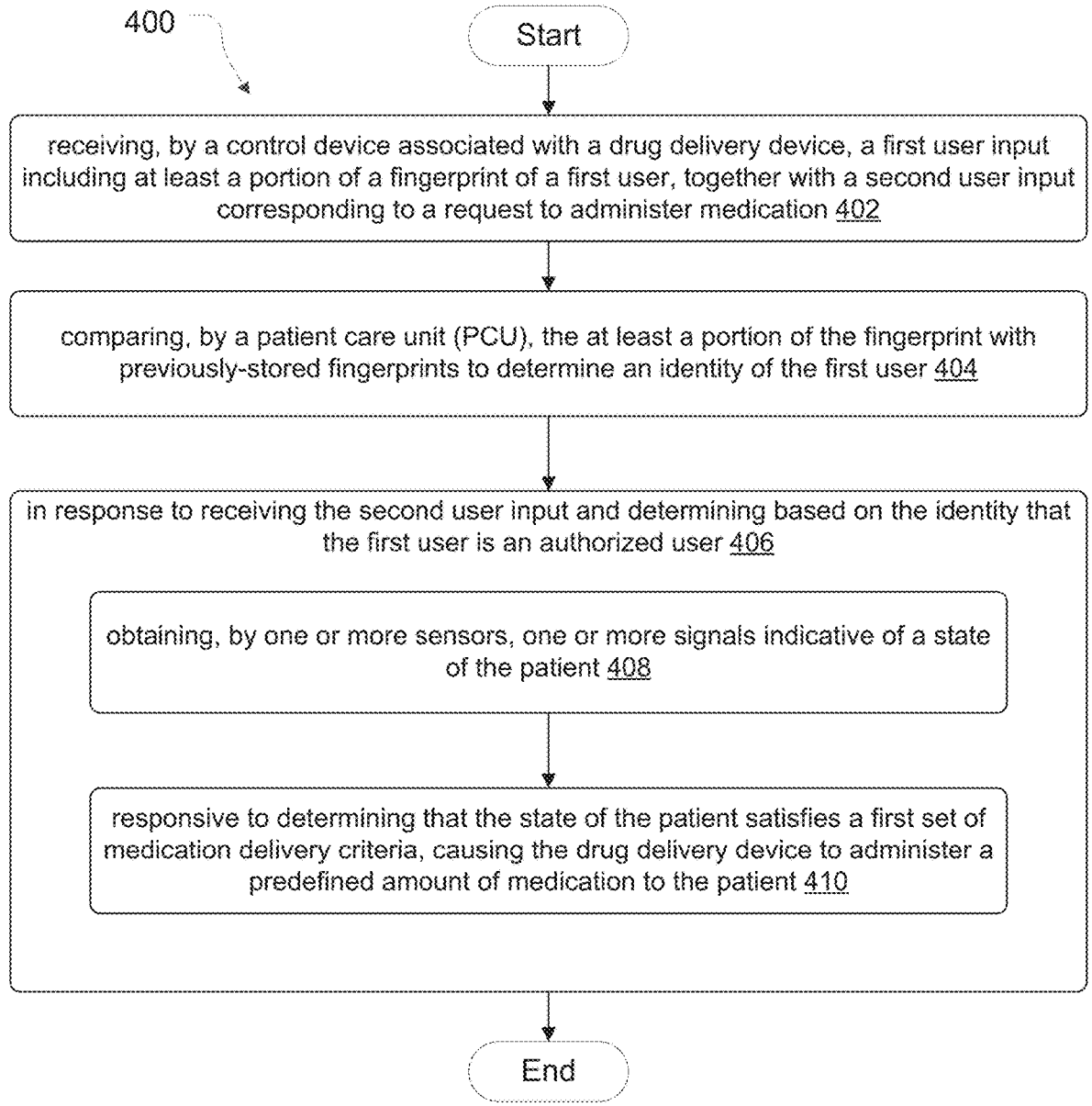
FIG. 4 depicts an example process for operating a patient care device, according to aspects of the subject technology.

Typically, medical fluid administration sets have more parts than are shown in FIG. 2A. Many have check valves, drip chambers, valved ports, connectors, and other devices well known to those skilled in the art. These other devices have not been included in the drawings so as to preserve clarity of illustration. For example, patient care device 200 may include a patient-controlled analgesia (PCA) device that allows patient 48 to self-administer medication (e.g., analgesics). Refer to FIGS. 3-4 and the related description below on how a PCA device can be operated.

Figure 2B:
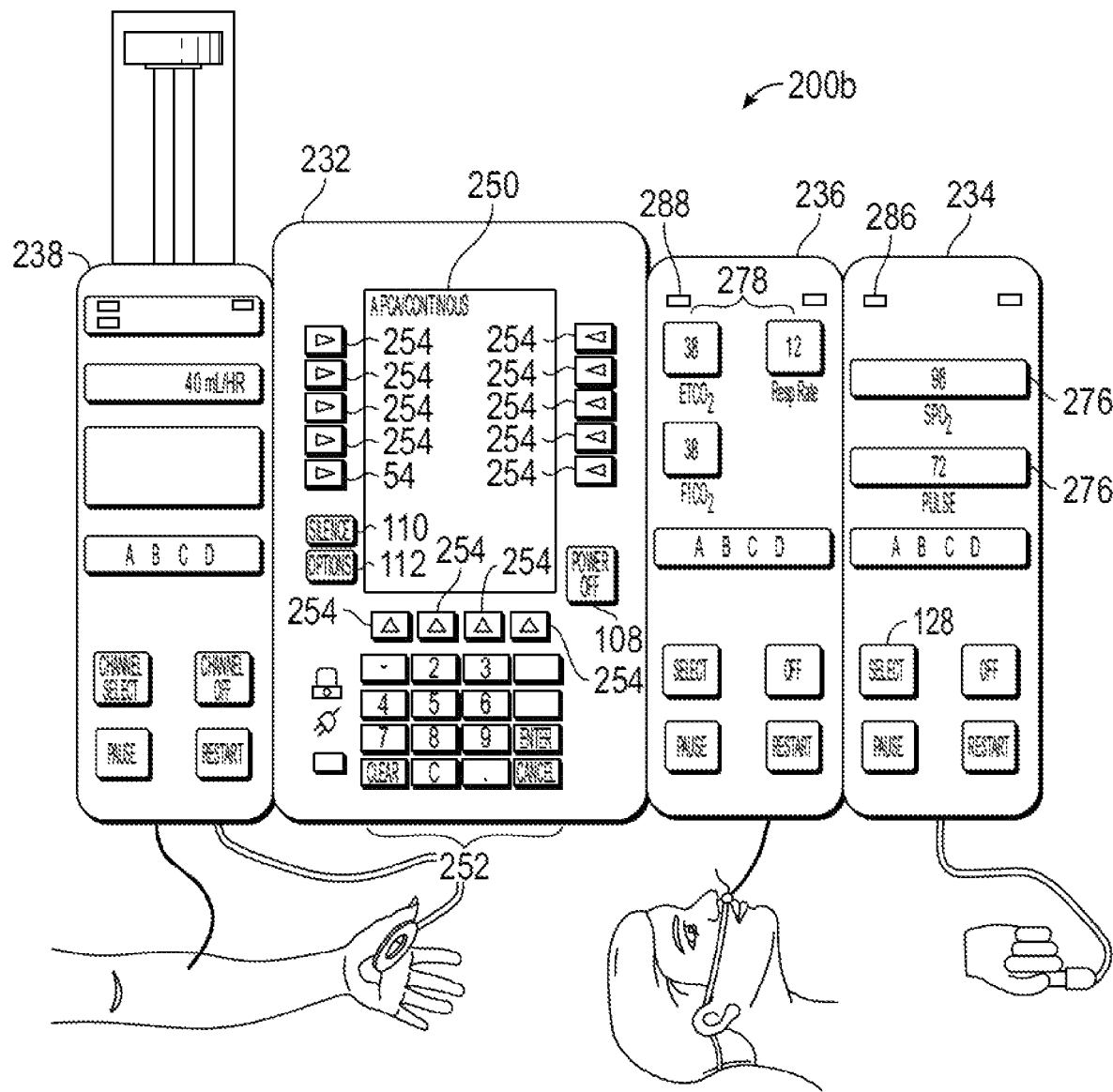
FIG. 2B is an elevation diagram showing the use of a controller in operational connection with a PCA pump, an EtCO2 monitoring module, an SpO2 monitoring module, a central server, and showing actual patient interaction with the system.

FIG. 2B is an elevation diagram showing the use of a controller in operational connection with a PCA pump, an EtCO2 monitoring module, an SpO2 monitoring module, a central server, and showing actual patient interaction with the system. Program module 232 includes memory and programs and, as an embodiment, may be described in terms of the advanced interface unit (100) found in U.S. Pat. No. 5,713,856 to Eggers incorporated herein by reference. The program module generally performs four functions in patient care system 200b. It provides a physical attachment of system 200b to structures such as IV poles and bed rails. It provides power to system 200b. It provides an interface between system 200b and external devices, and, except for certain specific information, it provides a majority of the user interface with system 200b.

Program module 232 contains information display 250, which may be any type of display such as a liquid crystal display. The display may be used during setup and operating procedures to facilitate data entry and editing. The display may also be used to display various operating parameters such as volume to be infused (VTBI) for individual infusion pump functional modules 238 and the current time of day, as well as other prompts, advisories, and alarm conditions. Program module 232 contains a plurality of hard keys 252 and soft keys 254 for entering data and commands. The numerical hard keys are used for entering numerical data, while the remainder of the hard keys, as well as the soft keys, are used for entering operational commands.

It is to be further understood that the functional modules, such as SpO2 module 234 and the EtCO2 module 236, in this embodiment also have processors and memory. Identification information must always be stored in the memory of each functional module. The identification information includes a means for uniquely identifying each functional module, preferably a serial number, so that, for example, the event history of each functional module can be followed and uploaded. The identification information also includes a means for identifying to program module 232 the function of the functional module, such as a code to indicate that the functional module is, for example, a PCA pump. This information allows program module 232 storing a plurality of software domains to know which domain to access for the selected functional module. Thus, the identification information stored in each functional module not only uniquely identifies the functional module to an attached interface module, but identifies the functions of the functional module as well. This identification information, as well as the software domain corresponding to a type of functional module comprises information specific to each functional module.

Functional modules, especially when they are physiological monitors, may contain their own internal programs in their own memory. For example, certain SpO2 and EtCO2 monitors are distributed by manufacturers in the form of a sensor with an accompanying "board" sold as a set. The accompanying board includes a processor, memory, and programming for processing the associated sensor's data. The board is typically located in functional monitor module 234 and 236 for example and is capable of providing data for a display and for alarms. Examples of such displays are shown in FIG. 2B where both functional modules 234 and 236 display data 276 and 278 respectively associated with their particular sensors. Such sensor/board sets include their own sets of rules for processing data produced by their respective sensors including rules concerning when to provide alarms. However, they may not provide specific processing for pausing a PCA module based on the sensor's data. In the past, alarms provided by the sensor/board set may have been used to pause a PCA pump. Such pausing based on the internal processor, programming, and rules of the sensor and board set for providing alarms have resulted in false alarms and unnecessary pausing, as discussed in the Background section of this document.

In accordance with an aspect of the invention, individual patient monitoring modules 234 and 236 may be configured to alarm distinctly and apart from the PCA Control Protocol alarming configuration. Such alarms may take the form of lights on the front panels of the monitoring modules 234 and 236 and may be audible as well. The alarms may also be transmitted to a remote server directly and independently by the monitoring modules or through a controller through a wired or wireless connection with the server. Additionally, the PCA Control Protocol may retrieve and consider data obtainable from the remote server such as patient lab data and pre-existing conditions of the patient, such as chronic obstructive pulmonary disease ("COPD"). For example, the PCA control protocol may be initially set to relatively low PCA pause limit levels when the server provides data indicating that the patient has COPD. The clinician may then alter the PCA pause limits and rules of the PCA control protocol through an input device such as a PDA or keyboard or other data communication device if desired based on actual observations of patient condition and reactions to PCA. Further, the PCA Control Protocol's initial rules and/or configuration may be altered or optimized by the central server based on additional information the central server possesses concerning the patient or rules or other.

The sets of rules in monitor modules 234 and 236 are allowed to proceed in their normal operation of the monitor modules and they may provide alarms based on their internal rule sets. Individual monitoring modules 234 and 236 could be disconnected from program module 232 and therefore also from the PCA Control Protocol by shutting down and/or removing the module. However, this method would have the disadvantage of not allowing the flexibility of letting the monitoring units continue their normal operation, including alarming, outside the PCA Control Protocol while avoiding nuisance pauses of the PCA infusion. Further in another embodiment, the PCA Control Protocol could alarm and pause PCA administration based on instantaneous values (non-filtered) from patient monitoring modules 234 and 236 as a backup. This method has the drawback of being subject to transient, short term fluctuations in monitoring data causing the PCA Control Protocol to create nuisance alarms and pauses.

FIG. 3 depicts an example of a patient controlled analgesia (PCA) device (also known as a PCA wand) 300, according to aspects of the subject technology. For example, PCA device 300 may be integrated with, or a part of, patient care device 12 or a module of patient care device (e.g., functional unit 16 of patient care device 12 in FIG. 1). When an input is received via PCA device 300, patient care device 12 is configured to activate one or more infusion devices (e.g., activating an infusion pumps to prepare and deliver medication) based on the received user input. Although various implementations are directed towards the use of biometric information (e.g. fingerprints) to authenticate a patient for the self-administering of analgesics, the subject technology is not limited to such and could include using other biometric-based authentication (e.g., passcode, facial recognition, etc.) for self-administering of any type of medication.

In some implementations, PCA device 300 includes a housing 306 that houses various electronics and wiring for implementing the functions of the fingerprint authentication. For example, a biometric sensor 302 may be integrated into the body PCA device 300. Biometric sensor 302 is configured to collect biometric signals of a user to determine the identity of the user. Biometric sensor 302 may be a fingerprint reader configured to capture an image of at least a portion of a user's fingerprint. On capturing the image, PCA device 300 sends the captured image of the user's fingerprint to the patient care unit either through a wired connection (e.g., wiring 310) or wirelessly for the patient care unit to determine whether the user is an authorized user to operate the patient care unit. In some implementations, the captured biometric information includes a retina scan.

According to some implementations, the biometric information is required to be captured within a predetermined period of time of the request (e.g. within a ten seconds or simultaneously) to administer a dose of medication for the request to be valid. In some implementations, biometric sensor 302 is integrated into PCA device 300 such that a user may activate button 304 and biometric sensor 302 will automatically collect the user's fingerprints when the button is pressed. For example, biometric sensor 302 and button 304 may be integrated as a single component within housing 306. Button 304 may be a physical button (e.g., a mechanical press button) or a virtual button (e.g., a user interface element shown on a touch-sensitive screen), and is configured to control one or more functional units of the patient care device (e.g., functional unit 18 of patient care device 12 in FIG. 1). For example, a user may press button 304 to cause an infusion pump (e.g., as a functional module of the patient care device) to dispense a predefined amount of medication to a patient (e.g., through intravenous delivery). The amount of medication administered may be based on a magnitude of the force applied to the button when pressed (e.g., a longer or a harder (e.g., higher pressure) press may cause a larger amount of medication to be administered). The amount of medication administered may be additionally or alternatively based on a frequency of button presses. In some implementations, if the user operating PCA device 300 is determined to not be authorized to administer medication, PCA device 300 may provide an alert (e.g., visual or audio) and not administer the medication.

In some implementations, the assessment of whether the medication is to be administered is being performed at PCA device 300 (e.g., by the processors and memory installed on PCA device 300). For example, if the user is determined to be an authorized user, the PCA request is transmitted to a patient care unit coupled to PCA device 300 or a PCA module (e.g., functional module 234 or 236 of FIG. 2B). On the other hand, if the user is determined to be an unauthorized user, the request is not further processed, but the attempt may be logged by the patient care unit or the PCA module. One or more feedbacks such as a visual or audio alarm may be set off at PCA device 300 due to the failed attempt.

In some embodiments, the assessment of whether the medication is to be administered is being performed by the PCA module. The PCA module receives the request to administer medication by PCA device 300, and determines whether the user is an authorized user. If the request is valid, the PCA module then forwards the request to the patient care unit, which causes a drug delivery device to administer a predetermined amount of medication. On the other hand, if the user is an unauthorized user, the request is not further processed and one or more feedback such as a visual or audio alarm may be set off at PCA device 300 or the PCA module. The failed attempt may be logged by the patient care unit of the PCA module.

For example, a patient may attempt to self-administer multiple doses or a single dose that exceeds a maximum amount of medication for a particular time period. In this regard, a second request for the drug delivery device to administer another dose of the medication may be received, and the system (e.g. control unit 14 or associated server) may determine, based on the second request, that the patient is not authorized to self-administer another dose of the medication from the drug delivery device. A feedback circuit within PCA device 300 provides the sensory information (e.g. an alarm) to the patient indicating that another dose will not be administered responsive to the second request.

In some embodiments, the assessment of whether the medication is to be administered is being performed by the patient care unit. Each request to administer medication, along with the captured biometrics of the user (e.g., fingerprints), are transmitted from PCA device 300 to the patient care unit. If the request is valid, the patient care unit administers the predetermined amount of medication. On the other hand, if the request is an invalid request, the patient care unit may log the unauthorized attempt and set off a visual or audio alarm at the patient care unit, the PCA module, or the PCA device.

In some implementations, patient care device 12 is communicably coupled to a database (e.g., database 137 in FIG. 1) storing a set of fingerprints, and upon receiving the fingerprints obtained by PCA device 300, patient care device 12 (or central server) compares the collected fingerprints to fingerprint profiles previously-stored in the database. In some implementations, fingerprint profiles for multiple users may be stored in the database as authorized to control PCA device 300 for a patient, including the patient him/herself, physicians, nurses, and caregivers who have been authorized to treat the patient.

In some implementations, upon successful fingerprint authentication (or other biometric-based authentication), the subject technology may require one or more additional administering criteria (not shown in FIG. 3) to be met before the patient care device can administer medication to the patient. For example, PCA device 300 may include or be connected with additional sensors for collecting signals related to the current status of the patient. These additional sensors may include motion sensors, EEG sensors, ECG sensors, SpO2 sensors, heart rate monitors, breath count sensors, sound sensor (e.g., microphone), and so on. The additional sensors may be connected directly to patient care device 12, or may transmit senor data to patient care device 12 over a wireless connection (e.g., using WiFi or BLUETOOTH, or the like). After successful fingerprint authentication, the patient care device administers medication to the patient only if the signals collected by the additional sensors indicate that the patient is in a condition suitable for receiving the medication. For example, if a motion sensor detects that the patient is in a moving condition, the patient care device may not administer medication for safety reasons. As another example, the sound sensor can be used to assess the patient's state of wakeness or level of pain. The assessment may be based on passive sound monitoring near the patient for an amount of noise (e.g., more noise likely indicates the patient is awake) or specific noises indicating a level of discomfort (e.g., groaning or sentiment analysis of spoken words). The assessment may be based on active sound monitoring whereby the patient responds to an automated prompt such as "What is your pain level?" The response may be interpreted by the system and provided as an input to the administration decision.

In some implementations, types of medication administration can be associated with a different set of authorizing criteria. For example, a first type of medication can only be administered if the EEG signals, the ECG signals, the SpO2 signals, heart rate, breath rate, sound, and motion signals satisfy a first set of criteria, and a second type of medication can only be administered if the EEG signals, the ECG signals, the SpO2 signals, heart rate, breath rate, sound, and motion signals satisfy a second set of criteria. In some implementations, the criteria may specify a subset of signals or alternative sets of signals that may authorize administration. For example, a drug or drug type may be administered if EEG signals adhere to the specified criteria or if breath rate corresponds to the criteria.

In some implementations, the patient (or another authorized user) may be legitimately requesting medication (e.g., the request satisfies the fingerprint authentication and the one or more additional criteria), but doing so too frequently. To prevent overdose, the patient care device 12 may implement a time-based lockout whereby the request is received but the drug delivery device takes no action until the lockout time elapses. For example, the lockout time may include a predetermined length of time between patient-initiated requests for a medication, or between a clinician-initiated bolus and a subsequent patient-initiated request. The length of the lockout period depends on the physical characteristics of the patient and the type of medication being requested.

FIG. 4 depicts an example process 400 for operating a patient care device, in accordance with aspects of the subject technology. In some implementations, the patient care device (e.g., patient care device 12 in FIG. 1) includes a drug control device (e.g., PCA device 300 in FIG. 3), a control unit (e.g., interface unit 14 in FIG. 3), and a drug delivery device (e.g., fluid infusion pump 22 in operative engagement with fluid administration set 30 in FIG. 2).

As the first step, the control unit 14 receives, from a control device (e.g., PCA device 300) associated with control unit 14 or associated module 16, 18, 20, 22 (e.g., a drug delivery device), a first user input including at least a portion of a fingerprint by a patient, together with a second user input corresponding to a request to administer medication (402). For example, the patient may provide the first user input and the second user input in one action, such as pressing a button integrated with a fingerprint reader, as illustrated in FIG. 3. The control device sends the at least a portion of a fingerprint and the request to administer medication to control unit 14. In other words, control unit 14 receives a request for the drug delivery device to administer a dose of the medication and biometric information captured by the drug control device.

Next, control unit 14 (or server 30 on behalf of control unit 14) compares the at least a portion of the fingerprint with previously-stored fingerprints to determine an identity of the patient (404). For example, when a patient is admitted, the patient's medical record may be updated with the patient's fingerprint(s) and stored in database 137. Patient care device 12 (or control unit 14 or module(s) 16, 18, 20, 22) may also be associated with the patient by the clinician, and that association also stored in database 137.

According to some implementations, PCA device 300 may be used to obtain the patient's fingerprint during an admission process, or when a clinician is preparing patient care device 12 to administer medication to the patient (e.g., at the patient's bedside). The clinician may scan his or her badge at control unit 14 to identify and authorize the clinician to initiate the administration of the medication, and scan an identification of the patient (e.g., a wristband barcode or RFID identifier) to associate the patient with the patient care device. The clinician may then be prompted by control unit 14 to impress the patient's fingerprint (or thumbprint) to biometric sensor 302 to enter the patient's fingerprint in the patient's stored electronic health record, or to verify that the correct patient is being associated with the pump (based on a previously-stored fingerprint associated with the patient in the record).

Patient care device 12 (or control unit 14 or module(s) 16, 18, 20, 22) may receive a portion of the medical record including, in some implementations, the patient's fingerprint, from server 30 or database 137. In some implementations, the fingerprint (or portion thereof) obtained by the control device is sent to the server, which identifies the patient based on the fingerprint. In this manner, or by the previously described association procedure undertaken by the clinician, the patient care device 12 (or PCU 14 or module(s) 16, 18, 20, 22) is associated with one or more authorized users, whose fingerprint profiles are stored in a database (e.g., database 137 in FIG. 1). Accordingly, when a request and fingerprint impression is received from the control device, the control unit 14 determines (e.g., by way of comparison 404) whether the patient is one of the authorized users associated with the patient to operate the patient care device to self-administer the medication.

In some implementations, the control unit 14 determines whether the patient is authorized to self-administer the dose of the medication from the drug delivery device. In this regard, the control unit 14 may determine the medication currently loaded by the drug delivery device. Such determination may merely be based on a prior entry of the medication identification or other associated parameter entry by the clinician at the drug delivery device (e.g. at interface device 54 or data input device 60). In some implementations, control unit 14 may query the server based on information available or received at the control unit (e.g. patient identifier or identifier associated with device 12 or control unit 14) to obtain the medication identification from the server. In some implementations, the request and biometric information obtained by the drug control device 300, and the device or patient identifier, are sent to the server, and the server determines whether the patient is authorized to self-administer the dose of the medication from the drug delivery device. In such implementations, the server informs the control unit 14 whether the patient is authorized.

In response to receiving the request to administer the medication (e.g., via the second user input) and determining based on the identity that the patient is an authorized user (406), the patient care device performs one or more additional verifications to identify a status of the patient before the medication is administered to the patient. For example, the additional verification(s) may include determining a state of the patient based on signals collected by one or more sensors integrated with or connected to the patient care device 12 (or patient control unit 14 or module(s) 16, 18, 20, 22). For detail on the one or more sensors and the collection of signals, refer to FIG. 3 and the related description.

To perform the additional verification, the one or more sensors obtain signals indicative of a state of the patient (408). These signals may be used to determine whether a state of the patient satisfies a predetermined criteria for allowing the patient to self-administer the medication. In some implementations, the one or more sensors are included in the drug control device. In some implementations, the sensors are activated after the request and biometric information are received by the drug control device (e.g., in response to the request and/or biometric information).

As described with regard to FIG. 3, the subject technology may be integrated with or connected to one or more motion sensors, EEG sensors, ECG sensors, SpO2 sensors, heart rate monitors, breath count sensors, and so on. In some implementations, signals obtained from these sensors may be compared to predetermined patterns or thresholds to determine whether the patient is experiencing a level of discomfort sufficient to warrant the requested administration of medication. In other words, the signals are compared to determine whether a state of the patient satisfies a set of medication delivery criteria. In one example, an EEG waveform may be determined from the sensor data and compared to predetermined waveforms indicative of one or more levels of discomfort. If the level of discomfort identified from the EEG waveform satisfies a predetermined threshold level of discomfort then the medication delivery criteria may be satisfied. In another example, an oxygen sensor may provide oxygen sensor data, which is then used to determine whether the patient is receiving a level of oxygen appropriate for administration of the particular medication provided by the patient care device 12. For example, a medication may be not be contraindicated for certain ranges of oxygen levels (e.g., below 85%). If the medication is not contraindicated for the current oxygen level of the patient then the request for a further administration of medication may be rejected.

In another example, a motion sensor may be used to determine a level of motion associated with the patient. For example, the motion sensor may be used to determine whether the patient is awake and moving (e.g., by sensing periodic movement or a level of movement per period of time above a certain threshold), or whether the patient is asleep (e.g., by sensing a lack of movement for a threshold period of time). If the patient is determined to be asleep then the requested administration of medication may be rejected. A level of movement may also be associated with a level of discomfort. In such a case, the requested amount of medication may only be delivered on sensing a level of movement, or a pattern of movement, associated with a threshold level of discomfort.

For example, the sensor(s) may be used (e.g. by the control unit or drug delivery device) to detect movement of the patient, and measure the physiological condition of the patient, and then determine the discomfort level based on the detected movement of the patient satisfying a movement threshold and the physiological condition satisfying a physiological threshold. The control unit and/or server and/or database may store different thresholds associated with different levels of discomfort. The different thresholds may be cross indexed to determine a current discomfort level of the patient based on current readings.

In some implementations, the amount of the requested medication may be automatically adjusted by the drug delivery device in accordance with the patient's determined level of discomfort. For example, if the patient is determined to be awake, but still and not in any discomfort based on sensor data (and/or based on other data, including level of motion, EEG or ECG patterns, SpO2 levels, heart rate, breathing data, or the like), the amount of medication to be delivered responsive to the request may be reduced. In some implementations, the amount may be adjusted proportionally (or based on a graduated scale) to the determined level of discomfort.

According to various implementations, if the medication delivery criteria is not met then an alert may be provided to a computing device associated with the clinician. For example, the alert may be sent by the PCU 14 (or the server 30 on behalf of the PCU) to a mobile device of the clinician. Additionally or in the alternative, the alert may be displayed on a display screen of the PCU or module associated with the requested medication administration, or provided audibly via a speaker integrated or associated with the PCU or module.

Responsive to determining that the state of the patient satisfies a set of medication delivery criteria, the drug delivery device administers a predefined amount of medication to the patient (410). As described previously, each medication may be associated with a different set of medication delivery criteria. For example, one medication may be delivered as long as the user is determined to be at rest (e.g., still), regardless of other signals. In another example, the medication can be delivered if the SpO2 level above a certain threshold and/or the heart rate is below a certain threshold.

In some implementations, determining that the state of the patient satisfies the set of medication delivery criteria may include determining that the patient is in a conscious state. Whether the patient is conscious or unconscious may, for example, be indicated by the EEG (with or ECG signals) collected from the patient.

In some implementations, determining that the state of the patient satisfies the set of medication delivery criteria may include determining that the patient has not received an amount of medication greater than a threshold amount in a past predefined period of time. That is to say, to prevent overdose, the patient care device implements a lockout period for administering medication. The length of the lockout period may be different for a different medication.

In some implementations, as described previously, determining that the state of the patient satisfies the first set of medication delivery criteria may include determining that a discomfort level associated with the patient is greater than a threshold discomfort level, and wherein the discomfort level associated with the patient is determined based on the one or more signals indicative of the state of the patient. For example, a comfort level may be calculated based on a combination of heart rate and breath rate of the patient.

In some implementations, administering, by the drug delivery device, the predefined amount of medication to the patient includes administering an amount of the medication in accordance with a magnitude of the second user input. For example, a longer press or a harder press on the control device would cause a larger bolus of medication to be administered, and a shorter press or a lighter press would cause a smaller bolus of medication to be administered.

Many of the above-described example 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
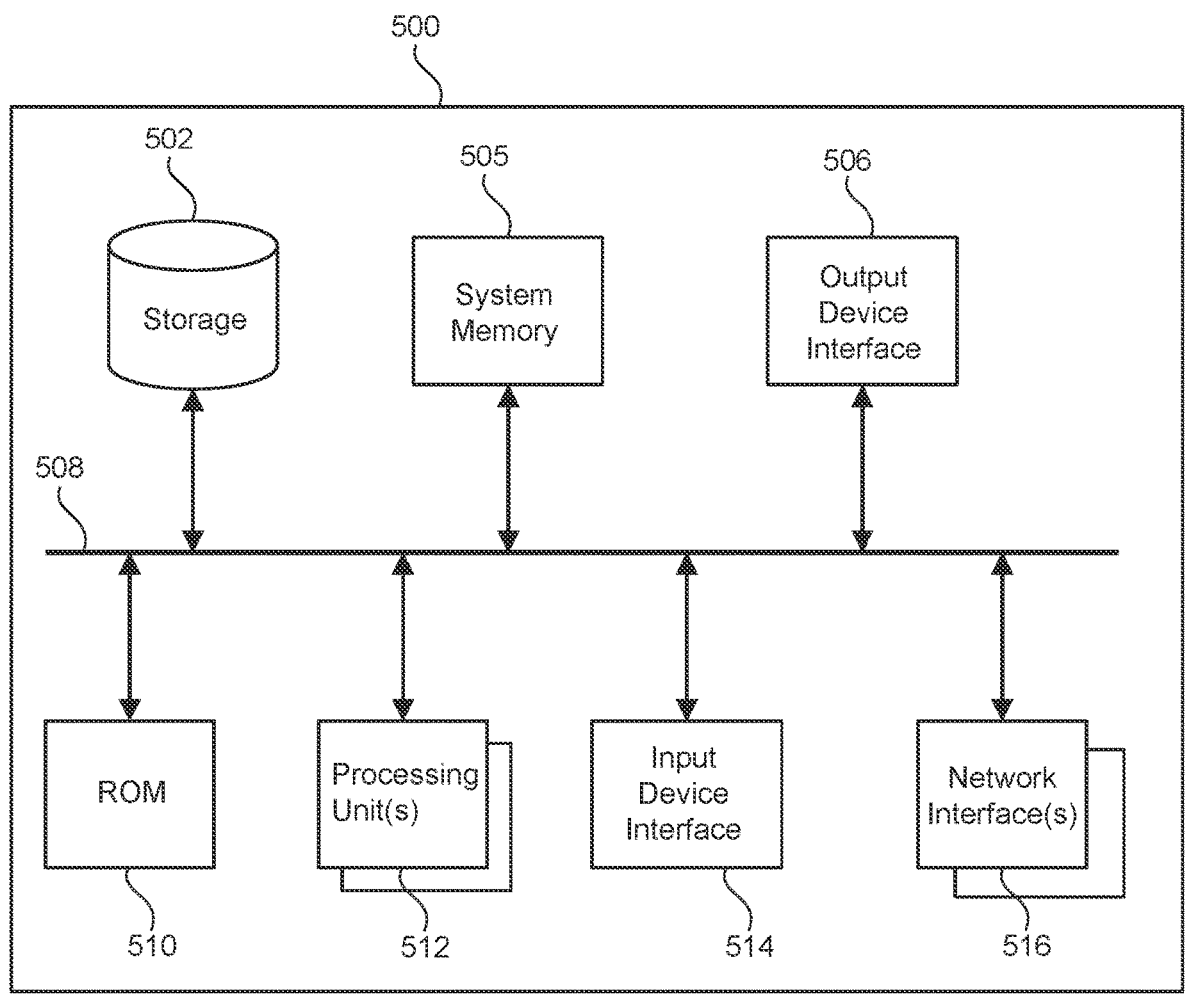
FIG. 5 is a conceptual diagram illustrating an example electronic system for operating an analgesia administration system, according to aspects of the subject technology.

FIG. 5 is a conceptual diagram illustrating an example electronic system 500 for operating an analgesia administration system, according to aspects of the subject technology. Electronic system 500 may be a computing device for execution of software associated with one or more portions or steps of process 400 of FIG. 1, or components and processes provided by FIGS. 1-3, including but not limited to information system server 30, computing hardware within patient care device 12, or device terminals 32. Electronic system 500 may be representative, in combination with the disclosure regarding FIGS. 1-4. In this regard, electronic system 500 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Other implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, as shown in FIG. 5, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples. A phrase such as an "embodiment" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

What is claimed is:

1. A system, comprising:
    a drug delivery device;
    a drug control device operably connected to the drug delivery device; and
    a control unit operably connected to the drug delivery device and configured to cause the drug control device to capture biometric information from a person,
    wherein the control unit is configured to:
        determine a medication currently loaded by the drug delivery device;
        receive, via the drug control device, a request for the drug delivery device to administer a dose of the medication and biometric information captured by the drug control device;
        confirm, based on the biometric information, that a patient associated with the biometric information is authorized to self-administer the dose of the medication from the drug delivery device; and
        responsive to receiving the request and biometric information and confirmation that the patient is authorized user to self-administer the dose:
            obtain, by one or more sensors associated with the drug delivery device, one or more signals indicative of a state of the patient; and
            cause, after determining that the state of the patient satisfies a predetermined criteria for allowing the patient to self-administer the medication, the drug delivery device to administer the dose of the medication to the patient.

2. The system of claim 1, wherein the drug control device is a handheld control device, and the request and biometric information are captured within a predetermined period of time of each other.

3. The system of claim 2, wherein the one or more sensors are included in the drug control device and activated after the request and biometric information are received by the drug control device.

4. The system of claim 1, wherein the drug control device comprises a fingerprint reader and the biometric information comprises a representation of at least a portion of a fingerprint captured by the fingerprint reader.

5. The system of claim 1, wherein the one or more signals indicative of the state of the patient include: an electroencephalogram (EEG) signal, electrocardiography (ECG) signal, peripheral capillary oxygen saturation (SpO2) signal, respiratory rate signal, or movement signal.

6. The system of claim 1, wherein determining that the state of the patient satisfies the predetermined criteria includes determining that the patient is in a conscious state based at least in part on the one or more signals.

7. The system of claim 1, wherein confirming that the patient is authorized to self-administer the dose comprises:
determining an identity of the patient;
identifying, from a hospital information system based at least in part on the identity of the patient or an identifier associated drug delivery device, an amount of medication received by the patient over a period of time; and
determining that the amount of medication satisfies a threshold amount for the period of time.

8. The system of claim 1, wherein the control unit is further configured to:
after obtaining the one or more signals indicative of a state of the patient, determining that a discomfort level associated with the patient is greater than a threshold discomfort level based on the one or more signals.

9. The system of claim 8, wherein the one or more sensors comprise:
a motion sensor for detecting movement of the patient; and
one or more physiological monitors for measuring a physiological condition, including: heart rate, blood pressure, electrocardiographic signal, electroencephalographic signal, or oxygen level,
wherein the control unit is configured to:
detect movement of the patient;
measure the physiological condition of the patient; and
determine the discomfort level based on the detected movement of the patient satisfying a movement threshold and the physiological condition satisfying a physiological threshold.

10. The system of claim 1, wherein the drug delivery device comprises a control configured to receive a user input to initiate the request, and to determine a magnitude of the user input, and wherein administering, by the drug delivery device, the dose of the medication to the patient includes administering an amount of the medication in accordance with the magnitude of the user input.

11. A machine-implemented method, comprising:
determining a medication currently loaded by a drug delivery device;
receiving, via a drug control device operably connected to the drug delivery device, a request for the drug delivery device to administer a dose of the medication and biometric information captured by the drug control device;
confirming, based on the biometric information, that a patient associated with the biometric information is authorized to self-administer the dose of the medication from the drug delivery device; and
responsive to receiving the request and biometric information and confirmation that the patient is authorized user to self-administer the dose:
obtaining, by one or more sensors associated with the drug delivery device, one or more signals indicative of a state of the patient; and
causing, after determining that the state of the patient satisfies a predetermined criteria for allowing the patient to self-administer the medication, the drug delivery device to administer the dose of the medication to the patient.

12. The machine-implemented method of claim 11, wherein the drug control device is a handheld control device, and the request and biometric information are captured within a predetermined period of time of each other.

13. The machine-implemented method of claim 12, wherein the drug control device comprises a fingerprint reader and the biometric information comprises a representation of at least a portion of a fingerprint captured by the fingerprint reader, and wherein the one or more sensors are included in the drug control device and activated after the request and the representation of at least a portion of a fingerprint of the patient are received by the drug control device.

14. The machine-implemented method of claim 11, wherein the one or more signals indicative of the state of the patient include: an electroencephalogram (EEG) signal, electrocardiography (ECG) signal, peripheral capillary oxygen saturation (SpO2) signal, respiratory rate signal, or movement signal.

15. The machine-implemented method of claim 11, wherein determining that the state of the patient satisfies the predetermined criteria includes determining that the patient is in a conscious state based at least in part on the one or more signals.

16. The machine-implemented method of claim 11, wherein confirming that the patient is authorized to self-administer the dose comprises:
determining an identity of the patient;
identifying, from a hospital information system based at least in part on the identity of the patient or an identifier associated drug delivery device, an amount of medication received by the patient over a period of time; and
determining that the amount of medication satisfies a threshold amount for the period of time.

17. The machine-implemented method of claim 11, wherein the one or more sensors comprise a motion sensor for detecting movement of the patient, one or more physiological monitors for measuring a physiological condition, including: heart rate, blood pressure, electrocardiographic signal, electroencephalographic signal, or oxygen level,
wherein the machine-implemented method further comprises:
detecting movement of the patient;
measuring the physiological condition of the patient; and
after obtaining the one or more signals indicative of a state of the patient, determining a discomfort level of the patient based on the detected movement of the patient satisfying a movement threshold and the physiological condition satisfying a physiological threshold, wherein the patient satisfying a predetermined criteria comprising the discomfort level satisfying a predetermined discomfort threshold.

18. The machine-implemented method of claim 11, wherein the drug delivery device comprises a control configured to receive a user input to initiate the request, and to determine a magnitude of the user input, and wherein administering, by the drug delivery device, the dose of the medication to the patient includes administering an amount of the medication in accordance with the magnitude of the user input.

19. A patient-controlled analgesic device for administering medication to a patient, comprising:
a fingerprint reader for obtaining at least a portion of a fingerprint of a patient;

an activation button for requesting a drug delivery device communicably coupled to the patient-controlled analgesic device to administer a predefined amount of medication to the patient;
one or more sensors for obtaining one or more signals indicative of a state of the patient;
a feedback circuit for indicating a working state of the patient-controlled analgesic device;
one or more processors; and
a memory including instructions that, when executed by the one or more processors, cause the one or more processors to perform operations comprising:
determining a medication currently loaded by a drug delivery device;
receiving, via the activation button, a request for the drug delivery device to administer a dose of the medication and a fingerprint of the patient captured by the fingerprint reader;
confirming, based on the fingerprint, that the patient is authorized to self-administer the dose of the medication from the drug delivery device;
responsive to receiving the request and biometric information and confirmation that the patient is authorized user to self-administer the dose:
obtaining, by one or more sensors associated with the drug delivery device, one or more signals indicative of a state of the patient; and
causing, after determining that the state of the patient satisfies a predetermined criteria for allowing the patient to self-administer the medication, the drug delivery device to administer the dose of the medication to the patient.

20. The patient-controlled analgesic device of claim 19, wherein the operations further comprise:
receiving a second request for the drug delivery device to administer another dose of the medication;
determining, based on the second request, that the patient is not authorized to self-administer another dose of the medication from the drug delivery device; and
providing, using the feedback circuit, sensory information to the patient indicating that another dose will not be administered responsive to the second request.

* * * * *